United States Patent [19]
Hewson

[11] Patent Number: 4,735,206
[45] Date of Patent: Apr. 5, 1988

[54] METHOD AND APPARATUS FOR DEFIBRILLATING AND PACING THE HEART

[75] Inventor: Carl E. Hewson, Marshfield, Mass.

[73] Assignee: Brunswick Manufacturing Co., Inc., Wareham, Mass.

[21] Appl. No.: 916,201

[22] Filed: Oct. 7, 1986

Related U.S. Application Data

[63] Continuation-in-part of Ser. No. 889,771, Jul. 28, 1986, abandoned.

[51] Int. Cl.$^4$ ............................................. A61N 1/36
[52] U.S. Cl. ........................ 128/419 D; 128/419 PG
[58] Field of Search ................... 128/419 D, 419 PG

[56] References Cited

U.S. PATENT DOCUMENTS

| | | | |
|---|---|---|---|
| 4,375,817 | 3/1983 | Engle et al. | 128/419 D |
| 4,407,288 | 10/1983 | Langer et al. | 128/419 D |
| 4,440,172 | 4/1984 | Langer | 128/419 D |
| 4,574,807 | 3/1986 | Hewson et al. | 128/419 PG |

Primary Examiner—William E. Kamm
Assistant Examiner—Timothy Keegan
Attorney, Agent, or Firm—Wolf, Greenfield & Sacks

[57] ABSTRACT

When the heart is in ventricular fibrillation, the heart cells that stimulate the heart muscles produce rapid repetitive excitation without coordinated contraction of the ventricle. There is no effective simultaneous action to make the heart beat in a rhythmic fashion. A defibrillator delivers to the heart cells and muscles, enough voltage to override the erratic voltages in the heart (called repolarization) so they can rearrange themselves with order. The heart can then start over to deliver a regular rhythm.

In accordance with the present invention, two small intimately located electrodes, one in the lower esophagus where it is intimate to the posterior section of the heart and the other small electrode on the chest over the sternum where it is close to the anterior portion of the heart, provide a precise electrical path between the two electrodes. A regulated power supply is turned on, and a relatively small voltage builds from zero over a period of approximately three-tenths of a second to its peak of approximately 150 volts. During this period, gentle repolarizing of the heart takes place. When the heart is repolarized, the heart cells become neutral. They are vulnerable to a stimulas. In accordance with a second embodiment of this invention, the defibrillation pulse is immediately followed by a stimulas in the form of pacing pulses that are at the rate of approximately 70 to 100 pulses per minute and of a magnitude of approximately 75 to 150 milliamps. The switch from one mode to the other is made without changing the location of the electrodes.

22 Claims, 4 Drawing Sheets

METHOD AND APPARATUS FOR DEFIBRILLATING AND PACING THE HEART

RELATED APPLICATION

This application is a continuation-in-part of my prior application Ser. No. 889,771 filed July 28, 1986 now abandoned entitled Method and Apparatus for Defibrillating the Heart.

FIELD OF THE INVENTION

This invention relates to a method and apparatus for defibrillating and pacing the heart.

BACKGROUND OF THE INVENTION

When a person's heart is in ventricular fibrillation, death is imminent. In ventricular fibrillation, the heart cells that stimulate the heart muscles are not coordinated so that although they stimulate the muscles, they produce rapid, erratic excitation without coordinated contraction of the ventricle. There is no effective simultaneous action to cause the heart to beat in a rhythmic fashion. To avoid death, immediate defibrillation is essential.

Defibrillation is achieved by delivering to the heart cells, enough voltage to override the erractic voltages in the fibrillating heart so that they can rearrange themselves with order. That action is called "repolarization". In this "repolarized" condition no heart action of any kind occurs for a peiod of three to eight seconds. After this three to eight seconds period, the heart cells arrange themselves to either fibrillate again or start a coordinated effort to beat on rhythm. If they fibrillate again, it is necessary to defibrillate them again, usually with more power. It may be necessary to do this several times before the heart cells arrange themselves to coordinate and beat in rhythm.

Defibrillation by high voltage is the accepted procedure today. Heavy duty equipment is required to deliver a very severe electric shock to the patient. The shock is delivered by placing two large paddle-type electrodes, each about three inches in diameter, at selected locations on the chest. By pressing down hard on the electrodes to make good electric contact with the skin, and by pressing a button provided on one of the paddle electrodes, the system is triggered so as to deliver the shock. The electrical shock is very abrupt; several thousand volts are impressed across the electrodes in a few milliseconds. In accordance with this procedure, in theory if the patient is given a large enough shock, some of it will pass through the heart and achieve repolarization. However, all the other muscles and nerves in the large area between the electrodes are also stimulated by the intense electrical shock, causing tremendous body flailing and thrashing.

SUMMARY OF THE INVENTION

The technique for defibrillating the heart in accordance with the present invention avoids the abusive effects of the high voltage techniques for defibrillation. In accordance with the present invention, two small intimately located electrodes are used, one in the lower esophagus intimate to the posterior section of the heart, and the other small electrode on the chest over the sternum close to the anterior portion of the heart. The electrodes provide a precise electrical path through the heart. An electrical circuit which may be a very small, lightweight and portable unit is connected across the electrodes so as to impress upon the electrodes a small voltage which increases from zero to a selected voltage up to 150 volts over a period of approximately three-tenths of a second after which time it is shut off. During the approximately three-tenths of a second time period, gentle repolarizing of the heart takes place. In this repolarized condition, no heart activity of any kind occurs for three to eight seconds. It is in a neutral, vulnerable condition for this long period of time, and on its own it may arrange to beat properly (rhythmn) or erratically (fibrillation). It is during this time that, in accordance with the present invention, the heart cells are influenced by pacing them with a controlled electrical pacing stimulation. This insures that the heart cells arrange for rhythmic beating instead of fibrillation.

The defibrillation device of this invention includes a relay which operates automatically, immediate following defibrillation, to direct pacing stimulas to the heart. The pacing unit may be a part of the design of the defibrillator or it may a be pacer embodying the features of the pacer shown in U.S. Pat. No. 4,574,807 dated Mar. 11, 1986 and entitled "Method and Apparatus for Pacing the Heart Employing External and Internal Electrodes".

Because relatively small voltages are used, during defibrillation the patient suffers no burns, minimal extraneous muscle action or other trauma, which frequently occur when the high voltage techniques are employed.

The internal electrode in the esophagus may be inserted through the mouth in the fashion of a gastric tube. The electrode itself may be of selected stiffness and flexibility so that it can be insreted directly into the esophagus. In the preferred embodiment, the electrode carries a plurality of circular contacts provided in the surface of the lower end of the tube. A stop may be carried on the other end of the electrode which will engage the face of the patient so as to prevent further electrode insertion when the distal end is in the proper location. The external electrode may be an ECG-type contact.

The portable electrical system connected to the electrodes preferably include a d.c. power supply, a timer circuit and some form of gate which over a period of approximately three-tenths of a second will allow the voltage impressed across the electrodes to increase from zero to a selected voltage up to 150 volts. The power supply includes a limiting circuit which will limit the current that flows between the electrodes to a selected amount up to approximately 150 to 200 milliamps. After the single three-tenths of a second surge of current flows between the electrodes, the defibrillator circuit shuts down, the relay operates and immediately a pacing pulse starts. The same internal and external electrodes are employed, and it is unnecessary to alter their positions. As taught in U.S. Pat. No. 4,574,807 supra, the pacing pulse preferably is a current of approximately 75 to 150 milliamps at a pulse rate of approximately 70 to 100 per minute. A separate circuit is provided for that purpose.

These and other objects and features of the present invention will be better understood and appreciated from the following detailed description read in connection with the accompanying drawings.

DETAILED DESCRIPTION OF THE INVENTION

Figure 1:
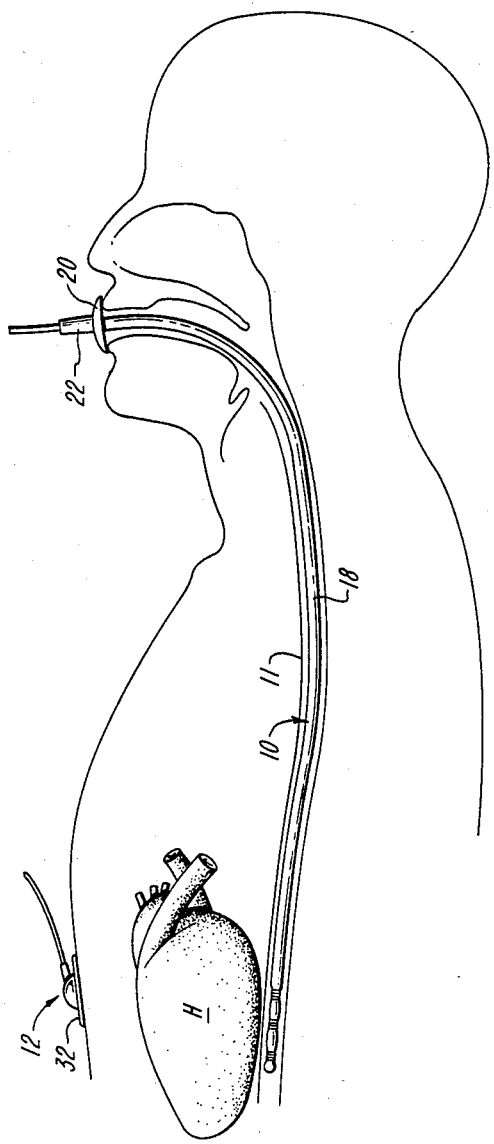
FIG. 1 is a cross-sectional view, somewhat diagrammatic, of the head and chest of a patient and showing the use of the present invention.

FIG. 1 depicts a patient being assisted by the defibrillating system and/or the defibrillating and pacing system combination of the present invention. A first electrode 10 is shown disposed in the patient's esophagus 11, and an external electrode 12 is shown placed on the patient's chest on the sternum. The electrodes are connected either to an electrical circuit 16 shown in FIG. 4, which impresses a voltage across the electrodes 10 and 12 so as to direct a small current through the heart for a period of three-tenths of a seconds or to a circuit 100 shown in FIG. 6, which will impress the short defibrillating pulse across the electrodes followed by a pacing pulse. The invention is hereafter described first as a defibrillating system and then as a system for both defibrillating and pacing the heart.

Figure 2:
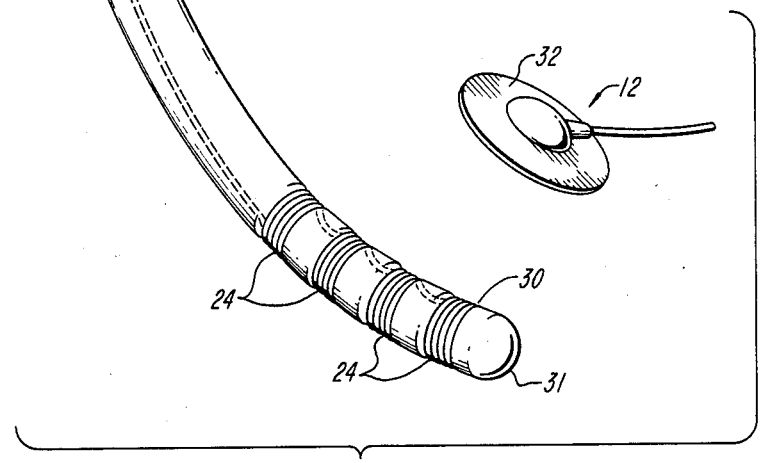
FIG. 2 is a perspective view of the two electrodes used to perform defibrillation in accordance with the present invention.

In FIGS. 1 and 2, the electrode 10 is shwon to include a curved, tubular body 18 which is shaped to be inserted directly into the patient's esophagus without the aid of a larger tubular member serving as a guide for that purpose. It is to be understood, however, that the system of the present invention may be used in combination with other apparatus, and it is contemplated that the electrode 10 in certain situations may be guided into the esophagus through a previously inserted tube such as a gastric tube. The electrode 10 carries a stop 20 at its proximal end 22 which may be used to limit depth of penetration of the electrode 10 into the esophagus. The stop 20 should not cover the mouth or otherwise interfere with the passage of air to and from the lungs.

The body of the electrode 10 preferably is somewhat flexible, in the nature of a commercially available gastric tube, so that it may be inserted in the esophagus and will not injure the esophageal lining. It may or may not call for the use of lubricant. Moreover, the electrode may be inserted through the mouth or nose. The electrode may be identical to that shown in U.S. Pat. No. 4,574,807, supra. The present applicant is a coinventor in that patent. The electrode is also shown in applicant's copending application Ser. No. 812,015, filed Dec. 23, 1985 and entitled "Method and Apparatus for Controlled Breathing Employing Internal and External Electrodes".

Figure 3:
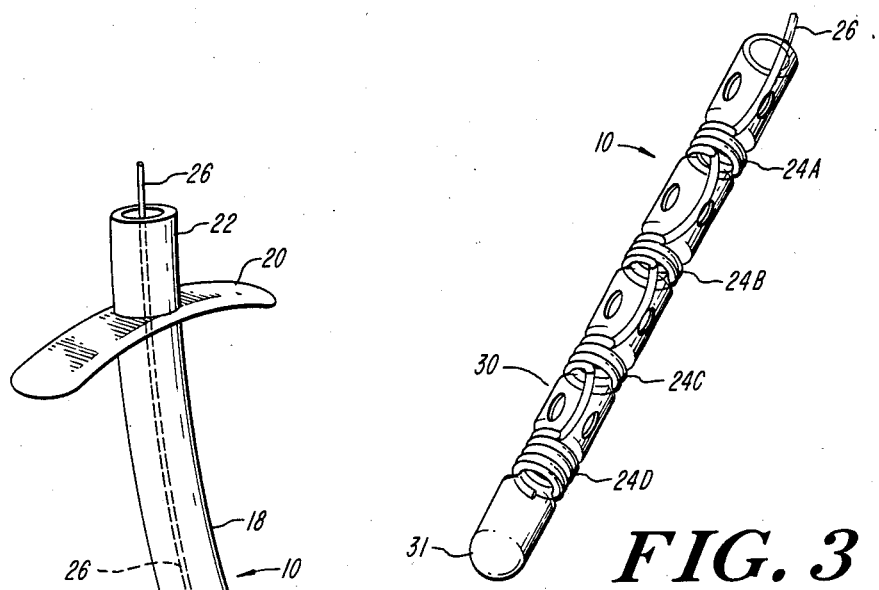
FIG. 3 is an enlarged perspective view of the distal end of the internal electrode shown in FIG. 2.

In FIG. 3, the distal end 30 of the electrode 10 is shown in detail. It includes four contact rings 24A-24D embedded in its surface. While four rings are shown, a lesser or greater number may be used. The contact rings in the embodiment shown are formed from a continuous length of tinned copper wire 26 which is connected to a post 28 carried on the body 18 and connected to the wire 26. The wire 26 extends inside the body 18 to first ring contact 24A, in turn formed by several turns of wire, on the surface of the body 18. The wire again enters the body 18 beyond the contact 24A and reemerges at the next ring contact 24B, also formed by several additional turns of wire. The third and fourth ring contacts 24C and 24D are similarly formed and connected to one another by the wire inside the body. Thus, the four electrode contacts are connected in series and formed from a single length of wire. Typically, each of the ring contacts may be 0.2-inch in length, and they may be spaced one inch apart. The wire may typically be 24-gauge. The distal end 30 of the body is provided with a smooth, rounded tip 31 which will slide smoothly down the esophagus or guide tube (if used).

When the electrode 10 is used to defibrillate the heart, the distal end 30 is positioned so that the several ring contacts 24 lie in the lower third of the esophagus intimate to the posterior section of the heart H. The stop 20 insures proper positioning of the electrode.

Figure 4:
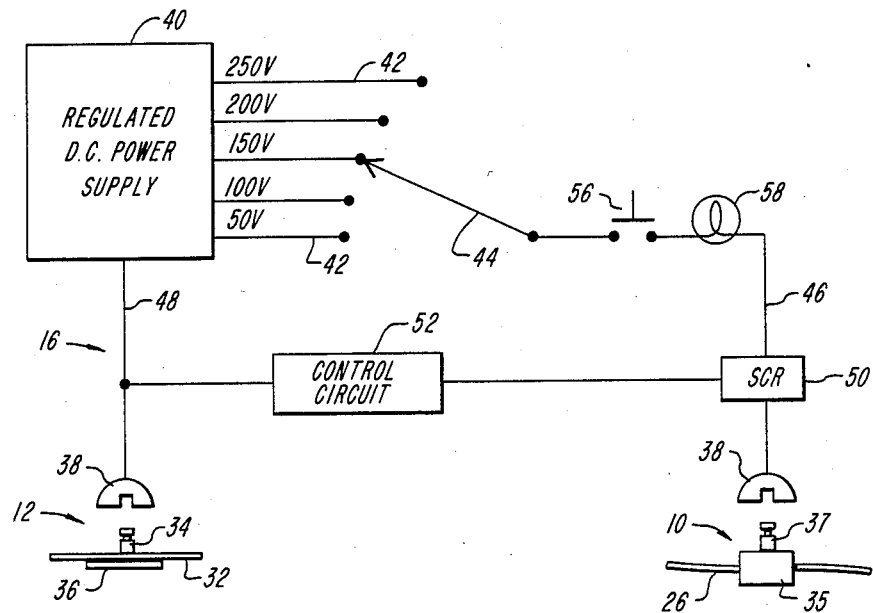
FIG. 4 is a schematic diagram of the electrical circuit of the invention used for defibrillation.

The external electrode 12 is like those used in electrocardiogram machines. As shown in FIG. 4, the electrode includes a flat, circular pad 32 with a post contact 34 on its upper surface connected to electrical contact 36 on its lower surface. A conducting gelatin is applied to the contact 36 when used to make good electrical contact with the patient's skin. The under surface of the pad 32 may also carry an adhesive to secure the electrode in place on the patient's chest above the sternum. While it presently appears that the optimal location for the external electrode is over the sternum, the invention is not limited to the precise location, and the external electrode may be placed elsewhere on the chest or upper abdomen, depending upon the frame of the patient.

The post contact 34 may be engaged by snap 38 which connects the electrode 12 to the electrical circuit 16. FIG. 4 also shows a connector 35 attached to the wire 26 of electrode 10 and which carries a post 37 that fits into snap 38.

The circuit 16 of FIG. 4 for impressing the voltage across the electrodes 10 and 12 includes a regulated d.c. power supply 40 with a 150 milliamp limit and with a series of voltage taps 42 connected to a selector switch 44 across the lines 46 and 48, in turn connected to the electrodes 10 and 12. A silicon control rectifier 50 is shown connected in line 46 and is also connected to the control circuit 52, which allows the voltage to climb from zero to a maximum value of approximately 150 volts as set on selector switch 44 and thereupon shut down the system. The circuit also includes an on/off switch 56 and an indicator light 58.

Figure 5:
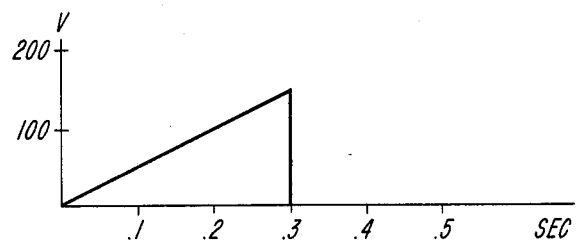
FIG. 5 is a chart of a single pulse imposed on the patient in accordance with this invention.

The voltage produced by the circuit 16 is illustrated in the chart of FIG. 5. In that figure, a single sawtooth pulse is shown, three-tenths of a second in duration and rising from zero to a maximum value of 150 volts. The voltage is limited by the voltage tap 42 selected by the switch 44 and a different maximum value may be selected. If it is desired to impress a second pulse on the patient, the switch 56 must again be closed. The limited current imposed by the power supply 40 insures that a maximum of 150 milliamps flows between the electrodes so that the esophagus is not injured.

It is apparent that the several contact rings 24 on the internal electrode 10 are each capable of defining the electrical path to the externally applied electrode 12 so that the continuously increasing current of limited value will flow between them and through the heart. The contact ring 24 on the internal electrode which defines the path of least resistance with the electrode 12 placed on the chest will complete the electrical circuit.

From the foregoing description, it will be appreciated that this invention makes possible the application of a defibrillating charge on an emergency basis by easily carried equipment and without subjecting the patient to the trauma normally imposed by the high voltage defibrillating systems. While an internal electrode is utilized, no invasive surgical procedure is required to place the internal electrode in position within the body of the patient.

Figure 7:
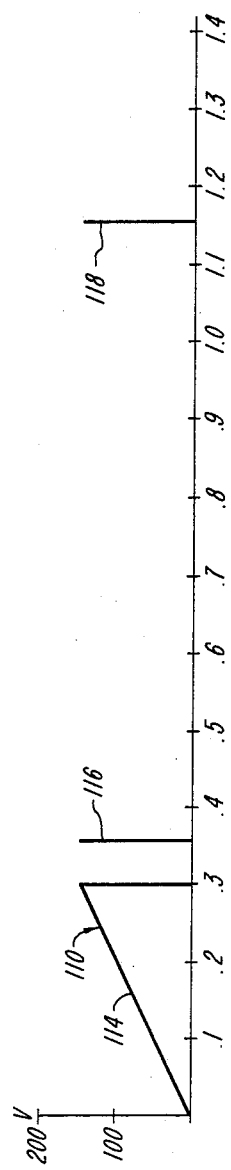
FIG. 7 is a chart of the defibrillation pulse and pacing pulse showing their relationship to one another.
Figure 6:
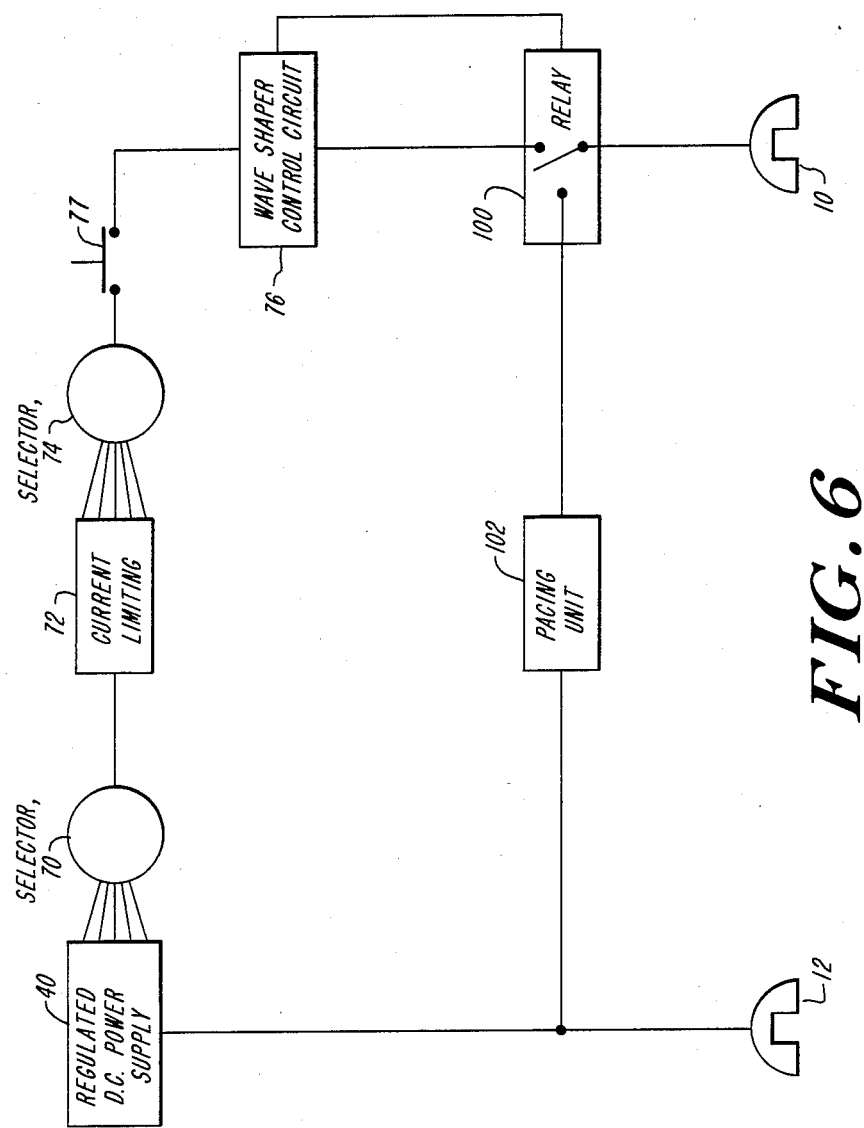
FIG. 6 is a schematic diagram of the electrical circuit of the invention used for both defibrillation and pacing.

In the embodiment of FIGS. 6 and 7, the embodiment of FIGS. 1-5 just described is combined with the apparatus of U.S. Pat. No. 4,574,807, supra, so as to provide a compact and portable heart conversion system by both defibrillating the heart and pacing it immediately upon successful defibrillation.

In FIG. 6 a defibrillating pulse circuit essentially the same as shown in FIG. 4 is combined with a pacing circuit, which may separately and selectively be connected to deliver a defibrillating pulse or pacing pulse across the electrodes 10 and 12. As in the circuit of FIG. 4, a regulated D.C. power supply 40 is shown, connected to a selector 70 which enables the operator to set the maximum voltage to be impressed across the electrodes 10 and 12. A current limiting circuit and selector 72 and 74 are also included, which enable the current value to be set by the operator. In the circuit shown, the wave shaper control circuit is represented by box 76. An on/off switch 77 is also shown.

A relay 100 is connected in the circuit, which automatically connects the pacing circuit 102 across the electrodes immediately after the defibrillating circuit 16 has delivered its pulse. The pacing circuit 102 may be like that shown in U.S. Pat. No. 4,574,807 supra, herein incorporated by reference, and include a low voltage d.c. source which may be much smaller and less powerful than the power supply 40, and a pulsing circuit. The pulsing circuit may also include a calibrated dial for adjusting the magnitude of the current from approximately 75 to 150 milliamps, either continuously or in steps. The pulse rate may also be adjusted by calibrated dial from approximately 70 to 100 pulses per minute. The duration of the pulse may be approximately one millisecond.

In FIG. 7 the relationship between the defibrillating pulse and the pacing pulses is shown. During the initial 0.3 second period, the defibrillating pulse 110 is represented by the ascending line 114 in the graph. Immediately after the defibrillating pulse is discontinued, the pacing pulse begins. Two spikes 116 and 118 are suggested, of very short duration, and at approximately 0.8 second intervals. These pulses will of course continue as long as required. Thus, the embodiment of FIGS. 6 and 7 is capable of first defibrillating and then immediately thereafter pacing the heart, by automatically actuating relay 100 and without changing the location of the electrodes. While capable of performing both functions, the system is nevertheless compact so that it may be easily transported and may very quickly be utilized to provide maximum care to the patient.

Having described the invention in detail, those skilled in the art will appreciate that numerous modifications may be made of it without departing from the spirit of this invention. Therefore, it is not intended that the breadth of this invention be limited to the specific embodiments illustrated and described. Rather, its scope is to be determined by the appended claims and their equivalents.

What is claimed is:

1. A method of defibrillating the heart of a patient comprising the step of
   impressing a voltage pulse to the heart having an initial value of zero and rising over approximately a three-tenths of a second period to a value in the order of 150 volts.

2. A method as defined in claim 1 further characterized by
   placing electrodes on opposite sides of the heart and imposing the voltage across the electrodes.

3. A method as defined in claim 1 further characterized by
   utilizing an ECG-type electrode placed on the chest of the patient.

4. A method of defibrillating the heart comprising the steps of
   placing a first electrode in the body posterior to the heart and a second electrode exterior of the body and anterior the heart, and
   impressing a voltage across the electrodes for a period of approximately three-tenths of a second and during which period the voltage goes from zero to a selected value of not more than 150 volts and then immediately returns to zero.

5. A method of defibrillating the heart comprising the steps of
   placing a first electrode having at least one contact internally in the lower third of the patient's esophagus,
   placing a second electrode having an ECG-type contact externally on the patient's chest in the region of the sternum with the contact in electrical communication with the patient's skin, and
   impressing a voltage across the internal and external electrodes for a period of approximately three-tenths of a second during which period the voltage increases from zero to a selected voltage of not more than 150 volts and returns to zero.

6. A method as defined in claim 5 further characterized by
   said external electrode being an ECG-type electrode.

7. Medical apparatus for defibrillating the heart comprising
   an elongated electrode member for insertion into the esophagus of the subject,
   a plurality of spaced-apart electrical contacts on the member for location in the lower third of the subject's esophagus when the member is inserted,
   a second electrode member having a contact for placement externally on the chest of the subject in electrical contact with the skin, and
   an electrical circuit including a power source connected to the electrode member for imposing a voltage across the member increasing over a period of approximately three-tenths of a second from zero a selected voltage of not more than 150 volts and thereafter immediately returning to zero volts.

8. Medical apparatus as defined in claim 7 further characterized by
   said electrical contacts on the elongated electrode member being ring contacts spaced longitudinally on said member.

9. Medical apparatus as defined in claim 8 further characterized by said contact of the second electrode member being an ECG-type contact.

10. Medical apparatus as defined in claim 7 further characterized by said contact of the second electrode member being an ECG-type contact.

11. A method of conversion of the heart from a fibrillation mode comprising the steps of
placing a first electrode in the body posterior to the heart and a second electrode exterior of the body and anterior the heart,
and impressing a defibrillating pulse and immediately after the defibrillating pulse impressing pacing pulses across the electrodes as part of the conversion.

12. A method as defined in claim 11 wherein the defibrillating pulse increases from zero to approximately 150 volts and returns to zero in a period of approximately three-tenths of a second.

13. A method as defined in claim 12 wherein the pacing pulses are at a rate of approximately 70 to 100 pulses per minute and at a magnitude of approximately 75 to 150 milliamps.

14. Medical apparatus for converting a fibrillating heart comprising
an elongated electrode member having at least one contact for insertion into the esophagus of the subject,
a second electrode member having a contact for placement externally over the sternum of the subject in electrical contact with the skin,
and an electrical circuit including a power source and connected to the electrode members for imposing a defibrillating pulse across the electrodes and immediately thereafter a series of pacing pulses across the electrodes as part of the conversion.

15. Apparatus as defined in claim 14 wherein the electrical circuit has a first part which generates a pulse for defibrillation having an initial value of zero and rising over approximately a three-tenths of a second period to a value in the order of 150 volts and a second part which generates a series of pacing pulses having a magnitude of approximately 70 at 150 milliamps,
and means for connecting the first part first and automatically the second part second to the electrodes.

16. A method of conversion of the heart from a fibrillation mode comprising the steps of
impressing a defibrillating pulse upon the heart to place the heart cells in a neutral condition,
and immediately after the defibrillating pulse impressing pacing pulses on the heart as part of the conversion.

17. Apparatus for converting a fibrillating heart comprising
a pair of electrodes which may be positioned adjacent the heart,
a first circuit connected to the electrodes for impressing a defibrillating pulse across the electrodes for placing the cells of the heart in a neutral condition,
a second circuit connected to the electrodes for impressing pacing pulses across the electrodes for pacing the heart,
and means connected to each of the circuits for activating the second circuit as part of the conversion immediately after the first circuit while the heart cells are in the nuetral condition.

18. A method of defibrillating the heart of a patient comprising the step of
impressing a voltage pulse to the heart having an initial value of zero and rising over approximately a three-tenths of a second period up to a selected value of not more than 150 volts.

19. Apparatus for converting a fibrillating heart comprising
means including a first circuit for impressing a defibrillating pulse upon the heart,
means including a second circuit for impressing pacing pulses upon the heart,
and means connected to each of the circuits for automatically activating the second circuit immediately after the first circuit so that the pacing pulses immediately follow the defibrillating pulse as part of the conversion.

20. Apparatus as defined in claim 19 wherein the first electrical circuit generates a pulse which in a period of three-tenths of a second increases from zero to a selected voltage up to 150 volts and returns to zero.

21. Apparatus as defined in claim 19 wherein the second circuit generates a series of pulses having a magnitude of approximately 70 to 150 milliamps.

22. Apparatus as defined in claim 20 wherein the second circuit generates a series of pulses having a magnitude of approximately 70 to 150 milliamps.

* * * * *